United States Patent
Shigemura et al.

(10) Patent No.: US 8,119,821 B2
(45) Date of Patent: Feb. 21, 2012

(54) SWEETENER COMPOSITIONS AND METHODS OF MAKING THEM

(75) Inventors: Rhondi Shigemura, Encinitas, CA (US); Carolyn Podgurski, San Diego, CA (US); Boriruck Kitisin, Carlsbad, CA (US); Maria Suparno, Jakarta Selatan (ID); Jennifer Ward, Spring Valley, CA (US); Thitiwan Lebien, Carlsbad, CA (US); Kevin Wirtz, Belgium, WI (US); James Robert Zeller, Holland, MI (US)

(73) Assignee: Senomyx, Inc., San Diego, CA (US)

(*) Notice: Subject to any disclaimer, the term of this patent is extended or adjusted under 35 U.S.C. 154(b) by 485 days.

(21) Appl. No.: 12/367,124

(22) Filed: Feb. 6, 2009

(65) Prior Publication Data
US 2009/0292010 A1    Nov. 26, 2009

Related U.S. Application Data

(60) Provisional application No. 61/026,640, filed on Feb. 6, 2008.

(51) Int. Cl.
*C07D 333/38* (2006.01)
(52) U.S. Cl. .......................................... 549/61
(58) Field of Classification Search .............. 549/61
See application file for complete search history.

(56) References Cited

U.S. PATENT DOCUMENTS

| 3,960,860 A | 6/1976 | Katz et al. |
| 4,535,081 A | 8/1985 | Kadin |
| 2007/0178123 A1 | 8/2007 | Levenson et al. |
| 2007/0275984 A1 | 11/2007 | Imogai et al. |

FOREIGN PATENT DOCUMENTS

| EP | 0082023 A2 | 6/1983 |
| WO | WO 2006/138512 A2 | 12/2006 |
| WO | WO 2008/154221 A2 | 12/2008 |

OTHER PUBLICATIONS

International Search Report based on International Application No. PCT/US2009/033395 (Jun. 10, 2009).
SENOMYX, Inc, Senomyx Announces Second Quarter 2007 Financial Results, Flexnews, Aug. 2007.
Leistner et al. "A facile synthesis of 2-Alkylthio-4-amino-thieno (2,3-d) pyrimidines", Jan. 1, 1989, Arch. Pharm. (Weinheim) 322:227-230.
Supplementary European Search Report based on European Patent Application No. EP 09709390 (Feb. 2, 2011).
European Search Opinion based on European Patent Application No. EP 09709390 (Feb. 2, 2011).

*Primary Examiner* — Taofiq A Solola
(74) *Attorney, Agent, or Firm* — Cooley LLP

(57) ABSTRACT

The present invention provides compositions comprising sucralose and 4-amino-5,6-dimethylthieno [2,3-d]pyrimidine-2(1H)-one or salts, solvates, and/or esters thereof and methods of making the compositions by spray drying. The present invention also provides ingestible compositions comprising compositions of the present invention and methods of making such foods. The present invention also includes a process of preparing 2-amino-thiophene derivatives, which are key intermediates for preparing 4-amino-5,6-dimethylthieno[2,3-d]pyrimidine-2(1H)-one.

8 Claims, No Drawings

SWEETENER COMPOSITIONS AND METHODS OF MAKING THEM

CROSS-REFERENCE TO RELATED APPLICATION

This application claims priority to U.S. Provisional Application No. 61/026,640, filed Feb. 6, 2008 and entitled "Sweetener Compositions and Methods of Making Them", the content of which is herein incorporated by reference in its entirety for all purposes. This application is also related to U.S. patent application Ser. No. 11/760,592, filed Jun. 8, 2007 and entitled "Modulation of Chemosensory Receptors and Ligands Associated Therewith"; U.S. patent application Ser. No. 11/836,074, filed Aug. 8, 2007 and entitled "Modulation of Chemosensory Receptors and Ligands Associated Therewith"; U.S. patent application Ser. No. 61/027,410, filed Feb. 8, 2008 and entitled "Modulation of Chemosensory Receptors and Ligands Associated Therewith"; and International Application No. PCT/US2008/065650, filed Jun. 3, 2008 and entitled "Modulation of Chemosensory Receptors and Ligands Associated Therewith". The content of these applications are herein incorporated by reference in their entirety for all purposes.

FIELD OF THE INVENTION

This invention relates to compositions comprising the combination of sucralose with 4-amino-5,6-dimethylthieno[2,3-d]pyrimidin-2(1H)-one, or salts, solvates and/or esters thereof, methods of making such compositions, and methods of making, e.g. ingestible products with such compositions. This invention also relates to processes of preparing 2-aminothiophene compounds.

BACKGROUND OF THE INVENTION

Obesity, diabetes, and cardiovascular disease are health concerns on the rise globally, but are growing at alarming rates in the United States. Sugar and calories are key components that can be limited to render a positive nutritional effect on health. High-intensity sweeteners can provide the sweetness of sugar, with various taste qualities. Because they are many times sweeter than sugar, much less of the sweetener is required to replace the sugar.

High-intensity sweeteners have a wide range of chemically distinct structures and hence possess varying properties, such as, without limitation, odor, flavor, mouthfeel, and aftertaste. These properties, particularly flavor and aftertaste, are well known to vary over the time of tasting, such that each temporal profile is sweetener-specific (Tunaley, A., "Perceptual Characteristics of Sweeteners", Progress in Sweeteners, T. H. Grenby, Ed. Elsevier Applied Science, 1989)).

Sweeteners such as saccharin and 6-methyl-1,2,3-oxathiazin-4(3H)-one-2,2-dioxide potassium salt (acesulfame potassium) are commonly characterized as having bitter and/or metallic aftertastes. Products prepared with 2,4-dihydroxybenzoic acid are claimed to display reduced undesirable aftertastes associated with sweeteners, and do so at concentrations below those concentrations at which their own tastes are perceptible. In contrast, some high-intensity sweeteners, notably sucralose (1,6-dichloro-1,6-dideoxy-β-D-fructofuranosyl-4-chloro-4-deoxy -α-D-galacto-pyranoside) and aspartame (N-L-α-aspartyl-L-phenylalanine methyl ester), display clean sweet tastes very similar to that of sugar (S. G. Wiet and G. A. Miller, Food Chemistry, 58(4):305-311 (1997)). In other words, these compounds are not characterized as having bitter or metallic aftertastes.

However, high intensity sweeteners such as sucralose and aspartame are reported to have sweetness delivery problems, i.e., delayed onset and lingering of sweetness (S. G. Wiet, et al., J. Food Sci., 58(3):599-602, 666 (1993)).

Hence, there is a need for compositions containing high intensity sweeteners with improved taste and delivery characteristics. In addition there is a need for foods containing high intensity sweeteners with such desirable characteristics.

SUMMARY OF THE INVENTION

In one embodiment, the present invention is directed to composition comprising a plurality of solid particles, each particle comprising sucralose and 4-amino-5,6-dimethylthieno[2,3-d]pyrimidine-2(1H)-one or salts, solvates, and/or esters thereof.

In another embodiment, the present invention is directed to a composition comprising a plurality of solid particles, each particle comprising sucralose and 4-amino-5,6-dimethylthieno[2,3-d]pyrimidine-2(1H)-one or salts, solvates, and/or esters thereof, prepared by spray drying a solution or dispersion comprising the sucralose and 4-amino-5,6-dimethylthieno[2,3-d]pyrimidine-2(1H)-one or salts, solvates, and/or esters thereof.

In yet another embodiment the present invention is directed to an ingestible product comprising sucralose and 4-amino-5,6-dimethylthieno[2,3-d]pyrimidine-2(1H)-one, or salts, solvates, and/or esters thereof.

In still another embodiment, the present invention is directed to a method of making a composition comprising solid particles, each particle comprising sucralose and 4-amino-5,6-dimethylthieno[2,3-d]pyrimidine-2(1H)-one, or salts, solvates, and/or esters thereof, said method comprising spray drying a solution or dispersion comprising the sucralose and 4-amino-5,6-dimethylthieno[2,3-d]pyrimidine-2(1H)-one or salts, solvates, and/or esters thereof.

In yet still another embodiment, the present invention is directed to a method of making an ingestible product, comprising combining sucralose and 4-amino-5,6-dimethylthieno[2,3-d]pyrimidine-2(1H)-thione, or salts, solvates, and/or esters thereof, with one or more edible ingredients.

In yet still another embodiment, the present invention is directed to a method of improving the sweetness delivery profile of a sucralose-containing ingestible composition, comprising incorporating into said sucralose-comprising ingestible composition 4-amino-5,6-dimethylthieno[2,3-d]pyrimidine-2(1H)-one, wherein 4-amino-5,6-dimethylthieno[2,3-d]pyrimidine-2(1H)-one:sucralose weight ratio ranges from about 1:2 to about 1:50.

In yet still another embodiment, the present invention is directed to a process of preparing a compound having structural Formula (a):

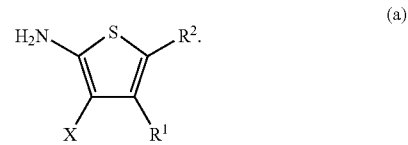

(a)

The process comprises mixing a compound having structural Formula (b):

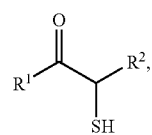

with a compound having structural Formula (c):

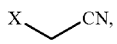

in the presence of an organic amine at a temperature of about 0° C. or below to obtain a reaction mixture; maintaining the reaction mixture at a temperature of about 0° C. or below for about 30 to about 90 minutes; concentrating the reaction mixture to obtain a slurry; and filtering the slurry to obtain the compound having structural Formula (a) as solid particles; wherein: $R^1$ is hydrogen, alkyl, heteroalkyl, aryl, heteroaryl, arylalkyl, or heteroarylalkyl; $R^2$ is hydrogen, alkyl, heteroalkyl, alkenyl, aryl, heteroaryl, arylalkyl, or heteroarylalkyl; or alternatively, $R^1$ and $R^2$, together with the atoms to which they are attached, form a carbocyclic ring or heterocyclic ring; X is CN or —C(O)$R^3$; $R^3$ is alkyl, aryl, heteroaryl, arylalkyl, heteroarylalkyl, O$R^4$, or N($R^4$)$_2$; and each $R^4$ is independently hydrogen, alkyl, aryl, heteroaryl, arylalkyl, or heteroarylalkyl.

DETAILED DESCRIPTION OF THE INVENTION

All documents cited in the present specification are incorporated by reference in their entirety for all purposes.

The compositions of the present invention comprise sucralose and 4-amino-5,6-dimethylthieno[2,3-d]pyrimidine-2(1H)-one or salts, solvates, and/or esters thereof. In one embodiment, the compositions of the present invention comprise a plurality of particles, e.g., in the form of a powder, wherein each of the particles comprises sucralose and 4-amino-5,6-dimethylthieno[2,3-d]pyrimidine-2(1H)-one or salts, solvates, and/or esters thereof.

As used herein, 4-amino-5,6-dimethylthieno[2,3-d]pyrimidine-2(1H)-one means the compound of formula (I):

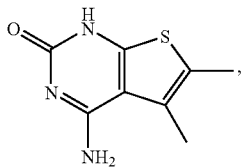

or salts, solvates, and/or esters thereof.

Compounds of formula (I) also includes tautomeric forms, including salts, solvates, and/or esters of the tautomeric forms. For example, a tautomeric form of formula (I) includes compounds of formula (Ia):

Salt(s) of 4-amino-5,6-dimethylthieno[2,3-d]pyrimidine-2(1H)-one refers to the product formed by the reaction of a suitable inorganic or organic acid with 4-amino-5,6-dimethylthieno[2,3-d]pyrimidine-2(1H)-one (as the "free base"). Suitable acids include those having sufficient acidity to form a stable salt, for example acids with low toxicity, such as the salts approved for use in humans or animals. Non-limiting examples of acids which may be used to form salts of 4-amino-5,6-dimethylthieno[2,3-d]pyrimidine-2(1H)-one include inorganic acids, e.g., HF, HCl, HBr, HI, $H_2SO_4$, $H_3PO_4$; non-limiting examples of organic acids include organic sulfonic acids, such as $C_{6-16}$ aryl sulfonic acids, $C_{6-16}$ heteroaryl sulfonic acids or $C_{1-16}$ alkyl sulfonic acids—e.g., phenyl, a-naphthyl, β-naphthyl, (S)-camphor, methyl, ethyl, n-propyl, i-propyl, n-butyl, s-butyl, i-butyl, t-butyl, pentyl and hexyl sulfonic acids; non-limiting examples of organic acids includes carboxylic acids such as $C_{1-16}$ alkyl, $C_{6-16}$ aryl carboxylic acids and $C_{4-16}$ heteroaryl carboxylic acids, e.g., acetic, glycolic, lactic, pyruvic, malonic, glutaric, tartaric, citric, fumaric, succinic, malic, maleic, hydroxymaleic, benzoic, hydroxybenzoic, phenylacetic, cinnamic, salicylic and 2-phenoxybenzoic acids; non-limiting examples of organic acids include amino acids, e.g. the naturally-occurring amino acids, lysine, arginine, glutamic acid, glycine, serine, threonine, alanine, isoleucine, leucine, etc. Other suitable salts can be found in, e.g., S. M. Birge et al., J. Pharm. Sci., 1977, 66, pp. 1-19 (herein incorporated by reference for all purposes). In one embodiment, salts of 4-amino-5,6-dimethylthieno[2,3-d]pyrimidine-2(1H)-one refers to salts which are biologically compatible or pharmaceutically acceptable or non-toxic, particularly for mammalian cells. In a particular embodiment, a suitable salt is 4-amino-5,6-dimethylthieno[2,3-d]pyrimidine-2(1H)-one hydrochloride. The salts of invention compounds may be crystalline or amorphous, or mixtures of different crystalline forms and/or mixtures of crystalline and amorphous forms.

Salt(s) of 4-amino-5,6-dimethylthieno[2,3-d]pyrimidine-2(1H)-one also refer to the product formed by the reaction of a suitable base with the tautomer of formula (1a). Non limiting examples of basic salts include, alkali metal salts such as the sodium and potassium salt; alkaline earth metal salts such as magnesium or calcium salts; transition metal salts such as ferric salts, etc.

Esters of 4-amino-5,6-dimethylthieno[2,3-d]pyrimidine-2(1H)-one include, e.g. esters formed by reacting the phenolic hydroxyl group of the tautomeric form (Ia) with an acid. For example, (1) carboxylic acid esters obtained by esterification of the phenolic hydroxyl group of a tautomer of 4-amino-5,6-dimethylthieno[2,3-d]pyrimidine-2(1H)-one, in which the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Solvates of 4-amino-5,6-dimethylthieno[2,3-d]pyrimidine-2(1H)-one refer to solid forms of 4-amino-5,6-dimethylthieno[2,3-d]pyrimidine-2(1H)-one in which one or more solvent molecules, for example water, are complexed to the 4-amino-5,6-dimethylthieno[2,3-d]pyrimidine-2(1H)-one.

The compositions of the present invention can consist only of 4-amino-5,6-dimethylthieno[2,3-d]pyrimidine-2(II)-one or salts, solvates, and/or esters thereof, and sucralose, or can include additional ingredients, e.g., one or more additional sweeteners.

In other embodiments, the sucralose can be admixed with the 4-amino-5,6-dimethylthieno[2,3-d]pyrimidine-2(1H)-one or salts, solvates, and/or esters thereof using conventional techniques such as dry blending, blending solutions/suspensions of the sucralose and 4-amino-5,6-dimethylthieno[2,3-d]pyrimidine-2(1H)-one or salts, solvates, and/or esters thereof, etc.

"Sweeteners" include, but are not limited to the common saccharide sweeteners, e.g., sucrose, fructose, glucose, and sweetener compositions comprising natural sugars, such as corn syrup (including high fructose corn syrup) or other syrups or sweetener concentrates derived from natural fruit and vegetable sources, semi-synthetic "sugar alcohol" sweeteners such as erythritol, isomalt, lactitol, mannitol, sorbitol, xylitol, maltodextrin, and the like, and artificial sweeteners such as aspartame, saccharin, acesulfame-K, cyclamate, sucralose, and alitame. Sweeteners also include cyclamic acid, mogroside, tagatose, maltose, galactose, mannose, sucrose, fructose, lactose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A and other sweet Stevia-based glycosides, carrelame and other guanidine-based sweeteners, etc. The term "sweeteners" also includes combinations of sweeteners as disclosed herein.

The compositions of the present invention provide an improved "sweetness delivery profile" for compositions (e.g., ingestible compositions) sweetened with sucralose. The compositions of the present invention provide a shorter sweetness onset and a shorter sweetness lingering period compared to conventional compositions with are sweetened with sucralose only, and do not contain the 4-amino-5,6-dimethylthieno[2,3-d]pyrimidine-2(1H)-one or salts, solvates, and/or esters thereof of the compositions of the present invention.

According to the present invention, "sweetness delivery profile" refers to a distinguishing characteristic of a sweetener which includes both the time period preceding sweetness onset ("onset period"), and the time period during which sweetness lingers ("lingering period").

According to the present invention, an "ingestible composition" includes any substance intended for oral consumption either alone or together with another substance. The ingestible composition includes both "foods" and "non-edible products". For example, the ingestible composition includes comestible compositions/products and medicinal compositions/products.

"Food" herein means any edible product intended for consumption by humans or animals, including solids, semi-solids, or liquids (e.g., beverages). The term "food" and the term "food and beverage" are herein used interchangeably.

A variety of classes, subclasses and species of foods are known. Examples of food and beverage products or formulations include, but are not limited to sweet coatings, frostings, or glazes for comestible products or any entity included in the Soup category, the Dried Processed Food category, the Beverage category, the Ready Meal category, the Canned or Preserved Food category, the Frozen Processed Food category, the Chilled Processed Food category, the Snack Food category, the Baked Goods category, the Confectionary category, the Dairy Product category, the Ice Cream category, the Meal Replacement category, the Pasta and Noodle category, and the Sauces, Dressings, Condiments category, the Baby Food category, and/or the Spreads category.

In general, the Soup category refers to canned/preserved, dehydrated, instant, chilled, UHT and frozen soup. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consommé) to sauces (cream or cheese-based soups).

"Dehydrated and Culinary Food Category" usually means: (i) Cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) Meal solutions products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

The Beverage category usually means beverages, beverage mixes and concentrates, including but not limited to, carbonated and non-carbonated beverages, alcoholic and non-alcoholic beverages, ready to drink beverages, liquid concentrate formulations for preparing beverages such as sodas, and dry powdered beverage precursor mixes. The Beverage category also includes the alcoholic drinks, the soft drinks, sports drinks, isotonic beverages, and hot drinks. The alcoholic drinks include, but are not limited to beer, cider/perry, FABs, wine, and spirits. The soft drinks include, but are not limited to carbonates, such as colas and non-cola carbonates; fruit juice, such as juice, nectars, juice drinks and fruit flavored drinks; bottled water, which includes sparkling water, spring water and purified/table water; functional drinks, which can be carbonated or still and include sport, energy or elixir drinks; concentrates, such as liquid and powder concentrates in ready to drink measure. The hot drinks include, but are not limited to coffee, such as fresh, instant, and combined coffee; tea, such as black, green, white, oolong, and flavored tea; and other hot drinks including flavor-, malt- or plant-based powders, granules, blocks or tablets mixed with milk or water.

The Snack Food category generally refers to any food that can be a light informal meal including, but not limited to Sweet and savory snacks and snack bars. Examples of snack food include, but are not limited to fruit snacks, chips/crisps, extruded snacks, tortilla/corn chips, popcorn, pretzels, nuts and other sweet and savory snacks. Examples of snack bars include, but are not limited to granola/muesli bars, breakfast bars, energy bars, fruit bars and other snack bars.

The Baked Goods category generally refers to any edible product the process of preparing which involves exposure to heat or excessive sunlight. Examples of baked goods include, but are not limited to bread, buns, cookies, muffins, cereal, toaster pastries, pastries, waffles, tortillas, biscuits, pies, bagels, tarts, quiches, cake, any baked foods, and any combination thereof.

The Ice Cream category generally refers to frozen dessert containing cream and sugar and flavoring. Examples of ice cream include, but are not limited to: impulse ice cream;

take-home ice cream; frozen yoghurt and artisanal ice cream; soy, oat, bean (e.g., red bean and mung bean), and rice-based ice creams.

The Confectionary category generally refers to edible product that is sweet to the taste. Examples of confectionary include, but are not limited to candies, gelatins, chocolate confectionary, sugar confectionary, gum, and the likes and any combination products.

The Meal Replacement category generally refers to any food intended to replace the normal meals, particularly for people having health or fitness concerns. Examples of meal replacement include, but are not limited to slimming products and convalescence products.

The Ready Meal category generally refers to any food that can be served as meal without extensive preparation or processing. The ready meal include products that have had recipe "skills" added to them by the manufacturer, resulting in a high degree of readiness, completion and convenience. Examples of ready meal include, but are not limited to canned/preserved, frozen, dried, chilled ready meals; dinner mixes; frozen pizza; chilled pizza; and prepared salads.

The Pasta and Noodle category includes any pastas and/or noodles including, but not limited to canned, dried and chilled/fresh pasta; and plain, instant, chilled, frozen and snack noodles.

The Canned/Preserved Food category includes, but is not limited to canned/preserved meat and meat products, fish/seafood, vegetables, tomatoes, beans, fruit, ready meals, soup, pasta, and other canned/preserved foods.

The Frozen Processed Food category includes, but is not limited to frozen processed red meat, processed poultry, processed fish/seafood, processed vegetables, meat substitutes, processed potatoes, bakery products, desserts, ready meals, pizza, soup, noodles, and other frozen food.

The Dried Processed Food category includes, but is not limited to rice, dessert mixes, dried ready meals, dehydrated soup, instant soup, dried pasta, plain noodles, and instant noodles.

The Chill Processed Food category includes, but is not limited to chilled processed meats, processed fish/seafood products, lunch kits, fresh cut fruits, ready meals, pizza, prepared salads, soup, fresh pasta and noodles.

The Sauces, Dressings and Condiments category includes, but is not limited to tomato pastes and purees, bouillon/stock cubes, herbs and spices, monosodium glutamate (MSG), table sauces, soy based sauces, pasta sauces, wet/cooking sauces, dry sauces/powder mixes, ketchup, mayonnaise, mustard, salad dressings, vinaigrettes, dips, pickled products, and other sauces, dressings and condiments.

The Baby Food category includes, but is not limited to milk- or soybean-based formula; and prepared, dried and other baby food.

The Spreads category includes, but is not limited to jams and preserves, honey, chocolate spreads, nut based spreads, and yeast based spreads.

The Dairy Product category generally refers to edible product produced from mammal's milk. Examples of dairy product include, but are not limited to drinking milk products, cheese, yoghurt and sour milk drinks, and other dairy products.

Exemplary foods include confectioneries, chocolate confectionery, tablets, countlines, bagged selflines/softlines, boxed assortments, standard boxed assortments, twist wrapped miniatures, seasonal chocolate, chocolate with toys, alfajores, other chocolate confectionery, mints, standard mints, power mints, boiled sweets, pastilles, gums, jellies and chews, toffees, caramels and nougat, medicated confectionery, lollipops, liquorice, other sugar confectionery, gum, chewing gum, sugarized gum, sugar-free gum, functional gum, bubble gum, cough drops, herbs, seeds, spices, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savory biscuits and crackers, bread substitutes, breakfast cereals, ready to eat cereals, family breakfast cereals, flakes, muesli, other cereals, children's breakfast cereals, hot cereals, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/uht milk, full fat long life/uht milk, semi skimmed long life/uht milk, fat-free long life/uht milk, goat milk, condensed/evaporated milk, plain condensed/evaporated milk, flavored, functional and other condensed milk, flavored milk drinks, dairy only flavored milk drinks, flavored milk drinks with fruit juice, soy milk, sour milk drinks, fermented dairy drinks, coffee whiteners, powder milk, flavored powder milk drinks, fruit juices, vegetable juices, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavored yoghurt, fruited yoghurt, probiotic yoghurt, drinking yoghurt, regular drinking yoghurt, probiotic drinking yoghurt, chilled and shelf-stable desserts, dairy-based desserts, soy-based desserts, chilled snacks, fromage frais and quark, plain fromage frais and quark, flavored fromage frais and quark, savory fromage frais and quark, sweet and savory snacks, fruit snacks, chips/crisps, extruded cereals and snacks, tortilla/corn chips, popcorn, pretzels, nuts, other sweet and savory snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, hot soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned-foods, frozen food, frozen processed red meat, frozen processed poultry, frozen processed fish/seafood, frozen processed vegetables, frozen meat substitutes, frozen potatoes, oven baked potato chips, other oven baked potato products, non-oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and seed oil, cooking fats, butter, margarine, spreadable oils and fats, functional spreadable oils and fats, sauces, dressings and condiments, tomato pastes and purees, bouillon/stock cubes, stock cubes, gravy granules, liquid stocks and fonds, herbs and spices, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow-on milk formula, toddler milk formula, hypoallergenic milk formula, prepared baby food, dried baby food, other baby food, spreads, jams and preserves, honey, chocolate spreads, nut-based spreads, yeast-based spreads, toppings, syrups, and edible compositions containing whey protein, soy protein, and other plant and vegetable based proteins.

In one embodiment, foods include alcoholic beverages, baby food, baby formula, baked goods, breakfast cereals, cheese, chewing gum, coffee whiteners, condiments and relishes, confectionary and frostings, crackers, dairy products, egg products, fats and oils, fish products, frozen dairy, frozen dinners, fruit ices, gelatins and puddings, grain mixtures, granulated sugar, gravies, hard candy, imitation dairy products, coffee, coffee products and coffee beverages, jams and jellies, meat products, milk products, non-alcoholic beverages, nut products, grains and grain products, poultry, processed fruits, processed vegetables, reconstituted vegetables, ready to eat meals, salad dressings, seasonings and flavors, snack foods, soft candy, soups, sugar substitutes, sweet sauce, sweetener blends, table top sweeteners, tea, tea products, and tea beverages.

In a particular embodiment, foods include table top sweeteners and beverages. Beverages include, but are not limited to, fruit juices, soft drinks, tea, coffee, beverage mixes, milk drinks, alcoholic and non alcoholic beverages.

According to the present invention, "non-edible products" include supplements, nutraceuticals, functional food products (e.g., any fresh or processed food claimed to have a health-promoting and/or disease-preventing properties beyond the basic nutritional function of supplying nutrients), pharmaceutical and over the counter products, oral care products such as dentifrices and mouthwashes, cosmetic products such as sweetened lip balms and other personal care products that use sucralose and or other sweeteners.

The term "edible ingredient" herein means any edible component or mixture of components of food or food products, for example the edible ingredients which would typically be found in a recipe for human or animal foods. Edible ingredients include natural and synthetic food components.

In general, over the counter (OTC) product and oral care product generally refer to product for household and/or personal use which may be sold without a prescription and/or without a visit to a medical professional. Examples of the OTC products include, but are not limited to Vitamins and dietary supplements; Topical analgesics and/or anesthetic; Cough, cold and allergy remedies; Antihistamines and/or allergy remedies; and combinations thereof. Vitamins and dietary supplements include, but are not limited to vitamins, dietary supplements, tonics/bottled nutritive drinks, child-specific vitamins, dietary supplements, any other products of or relating to or providing nutrition, and combinations thereof. Topical analgesics and/or anesthetic include any topical creams/ointments/gels used to alleviate superficial or deep-seated aches and pains, e.g. muscle pain; teething gel; patches with analgesic ingredient; and combinations thereof. Cough, cold and allergy remedies include, but are not limited to decongestants, cough remedies, pharyngeal preparations, medicated confectionery, antihistamines and child-specific cough, cold and allergy remedies; and combination products. Antihistamines and/or allergy remedies include, but are not limited to any systemic treatments for hay fever, nasal allergies, insect bites and stings. Examples of oral care product include, but are not limited to mouth cleaning strips, toothpaste, toothbrushes, mouthwashes/dental rinses, denture care, mouth fresheners at-home teeth whiteners and dental floss.

In another embodiment, foods include ice creams, breakfast cereals, sweet beverages or solid or liquid concentrate compositions for preparing beverages.

In various embodiments, edible compositions according to the present invention, comprising at least one edible ingredient, sucralose, and 4-amino-5,6-dimethylthieno[2,3-d]pyrimidine-2(1H)-one or salts, solvates, and/or esters thereof; wherein the edible ingredient includes baked goods and baking mixes, beverages, alcoholic beverages and beverage mixes, breakfast cereals, cheeses, chewing gum, coffee and tea, condiments and relishes, confections and frostings, dairy product substitutes, fats and oils, frozen dairy desserts and mixes, fruit and water ices, gelatins, puddings, and fillings, gravies and sauces, pet foods, hard candy and cough drops, herbs, seeds, spices, seasonings, blends, extracts, and flavorings, jams and jellies, meat products, milk products, processed fruits and fruit juices, processed vegetables and vegetable juices, snack foods, soft candy, soups and soup mixes, sugar substitutes, sweet sauces, toppings, and syrups, whey protein, soy protein, plant and vegetable based proteins, nutritional products & dietary supplements, pharmaceuticals, etc.

In other embodiments, edible compositions according to the present invention, comprising at least one edible ingredient, sucralose, and 4-amino-5,6-dimethylthieno[2,3-d]pyrimidine-2(1h)-one or salts, solvates, and/or esters thereof; wherein the edible ingredient includes alcoholic beverages, baby food, baby formula, baked goods, breakfast cereals, cheese, chewing gum, coffee whiteners, condiments & relishes, confectionery & frostings, crackers, dairy products, egg products, fats & oils, fish products, frozen dairy, frozen dinners, fruit ices, gelatins & puddings, grain mixtures, granulated sugar, gravies, hard candy, imitation dairy products, coffee, coffee products and coffee beverages, jams & jellies, meat products, milk products, non-alcoholic beverages, nut products, grains and grain products, poultry, processed fruits, processed vegetables, reconstituted vegetables, ready to eat meals, salad dressings, seasonings & flavors, snack foods, soft candy, soups, sugar substitutes, sweet sauce, sweetener blends, table top sweeteners, tea, tea products, and tea beverages.

The term "particles" herein means particles that have been formed from a solution or suspension by a spray drying process. The particles according to the present invention may be of any size. In one embodiment, the particles have a diameter of from about 20 μm to about 200 μm, e.g., from about 50 μm to about 175 μm, or from about 75 μm to about 150 μm. In another embodiment the spray dried particles can have substantially rounded shape, wherein about 40% to about 80% of the spray dried particles have a diameter of from about 20 μm to about 200 μm. Generally, the particles are within a more tightly controlled specific range whose limits depend upon the particular application for which the composition is intended.

Compositions of the present invention comprise a plurality of particles. The particles of the present invention can have any suitable particle size distribution, for example relatively large particles with a small proportion of small particles. The particle size distribution can be unimodal or multimodal (e.g., the combination of two or more different unimodal particle size distributions.

The particles of the present invention can be essentially spherical, or can have a non-spherical shape defined by a length to diameter (L/D) ratio which is greater than 1. In one embodiment, the particles generally have an L/D ratio in the range 5-10. In other embodiments, the L/D ratio can be about 1. Another useful characteristic is $d_{50}$, the spray droplet diameter that corresponds to the diameter of the droplets that make up 50% of the total liquid volume containing particles of equal or smaller diameter. In one embodiment, the droplets will have a $d_{50}$ between 100 and 1000 μm in size, as determined by a drop-size analyzer. In another embodiment of the invention, the particles have a $d_{50}$ between 400 and 800 μm in size, and are especially useful in dissolution applications. For producing substantially homogenous particles, the inventors have found that $d_{50}$ should be between 100 and 200 μM in size with an L/D ratio of less than 2.0.

The particles of the present invention, as indicated herein, can be prepared e.g., by spray drying a solution or suspension of sucralose and 4-amino-5,6-dimethylthieno[2,3-d]pyrimidine -2(1H)-one or salts, solvates, and/or esters thereof. The spray dried solution or suspension can contain only solvent, sucralose, and 4-amino-5,6-dimethylthieno[2,3-d]pyrimidine-2(1H)-one or salts, solvates, and/or esters thereof, or additionally contain a carrier such as maltodextrin, starches, gum Arabic, or other acceptable carriers or fillers known in the art.

In one embodiment of the present invention, spray dried particles, each comprising 4-amino-5,6-dimethylthieno[2,3-d]pyrimidine-2(1H)-one, or salts, solvates, and/or esters thereof and sucralose, have improved dissolution characteristics, or provide improved dissolution characteristics to the compositions comprising the particles of the present invention, compared to non-spray dried particles (e.g., prepared by mixing or granulation). For example, such improved dissolution properties include an increased dissolution rate.

The particles of the present invention may be in various densities depending on the intended use. In one embodiment of the present invention, the bulk density of the particles is between 0.25 and 0.75 g/mL. In another embodiment the bulk density of the particles is between 0.25 and 0.5 g/mL. In still another embodiment of the present invention, the particles have a moisture content between 0.25 and 0.5 wt %. In yet another embodiment, the particles have a moisture content between 0.4 and 0.5 wt %.

The particles of the present invention, comprising sucralose and 4-amino-5,6-dimethylthieno[2,3-d]pyrimidine-2 (1H)-one or salts, solvates, and/or esters thereof, can contain the 4-amino-5,6-dimethylthieno[2,3-d]pyrimidine-2(1H)-one or salts, solvates, and/or esters at a concentration of about 50 wt. % to about 85 wt. %, including about 55 wt. %, about 60 wt. %, about 65 wt. %, about 70 wt. %, about 75 wt. %, or about 80 wt. %, inclusive of all ranges and subranges therebetween.

4-Amino-5,6-dimethylthieno[2,3-d]pyrimidine-2(1H)-one or salts, solvates, and/or esters thereof used is useful for modulating (inducing, enhancing or inhibiting) the sweet taste or other taste properties of the sweeteners provided individually, or in combination with any food product. Reduction in sweetener with increasing amounts of 4-amino-5,6-dimethylthieno[2,3-d]pyrimidine-2(1H)-one or salts, solvates, and/or esters thereof maintains or enhances the sweetness profile of a sweetener-containing composition or food without compromising taste. Hence in one embodiment of the invention, the flavor of a sweetener, provided individually, or in combination with any food product is enhanced in the presence of 4-amino-5,6-dimethylthieno[2,3-d]pyrimidine-2(1H)-one or salts, solvates, and/or esters thereof.

It is recognized that the concentration of 4-amino-5,6-dimethylthieno[2,3-d]pyrimidine-2(1H)-one or salts, solvates, and/or esters thereof needed to improve the flavor of a food product will depend on many variables, including the specific type of food and its other ingredients, especially the presence of other known sweet flavoring agents, the genetic variability and individual preferences and health conditions of various human beings tasting the compositions, and the subjective effect of the particular compound on the taste of such chemosensory compounds. In one embodiment, the amount of 4-amino-5,6-dimethylthieno[2,3-d]pyrimidine -2(1H)-one or salts, solvates, and/or esters thereof, by weight, ranges from about 0.001 ppm to about 100 ppm of the food product. In another embodiment, the amount ranges from about 0.1 ppm to about 10 ppm of the food product.

The amount of 4-amino-5,6-dimethylthieno[2,3-d]pyrimidine-2(1H)-one or salts, solvates, and/or esters thereof in the composition, or in combination with a food product, can be measured in relation to the amount of sweetener (e.g., sucralose) present in the composition or the food product. In one embodiment, the 4-amino-5,6-dimethylthieno[2,3-d]pyrimidine-2(1H)-one or salts, solvates, and/or esters thereof: sweetener weight ratio is from about 1:50 (compound:sweetener) to about 1:10. In another embodiment, the 4-amino-5,6-dimethylthieno[2,3-d]pyrimidine-2(1H)-one or salts, solvates, and/or esters thereof: sweetener weight ratio is from about 1:30 to about 1:20.

In one embodiment of the present invention, spray dried particles, each comprising 4-amino-5,6-dimethylthieno[2,3-d]pyrimidine-2(1H)-one, or salts, solvates, and/or esters thereof and sucralose, have an improved sweetness delivery profile. In another embodiment of the present invention, the improvement comprises reducing the onset period of the sweetness delivery profile of a sweetener. In another embodiment, the improvement comprises reducing the lingering period of the sweetness delivery profile of a sweetener. In yet another embodiment, the improvement comprises reducing both the onset period and the lingering period of the sweetness delivery profile of a sweetener.

In another embodiment of the present invention, 4-amino-5,6-dimethylthieno[2,3-d]pyrimidine-2(1H)-one, or salts, solvates, and/or esters thereof induce shortening of sweetness onset and lingering periods of sucralose.

The ingestible composition whose sweetness delivery profile is improved can contain any sweetening amount of sucralose relative to 4-amino-5,6-dimethylthieno[2,3-d]pyrimidine-2(1H)-one or salts, solvates, and/or esters thereof. In one embodiment, the 4-amino-5,6-dimethylthieno[2,3-d]pyrimidine-2(1H)-one or salts, solvates, and/or esters thereof: sucralose weight ratio is from about 1:2 to about 1:50. In another embodiment, the 4-amino-5,6-dimethylthieno[2,3-d] pyrimidine-2(1H)-one or salts, solvates, and/or esters thereof: sucralose weight ratio is from about 1:5 to about 1:40. In yet another embodiment, the 4-amino-5,6-dimethylthieno[2,3-d]pyrimidine-2(1H)-one or salts, solvates, and/or esters thereof: sucralose weight ratio is from about 1:8 to about 1:20.

For baked goods (e.g., cookies), the weight ratio of 4-amino-5,6-dimethylthieno[2,3-d]pyrimidine-2(1H)-one or salts, solvates, and/or esters thereof: sucralose is about 1:10 to about 1:20, about 1:12, about 1:14, about 1:16, or about 1:18. For table top sweeteners, the weight ratio ranges from about 1:15 to about 1:30, about 1:17, about 1:19, about 1:20, about 1:22, about 1:24, about 1:26, or about 1:28. For beverages, the weight ratio ranges from about 1:5 to about 1:40; e.g., for hot cocoa the weight ratio ranges from about 1:20 to about 1:30, about 1:23, about 1:25, or about 1:27; for colas the weight ratio ranges from about 1:5 to about 1:10, about 1:7 or about 1:9. For frozen dairy products (e.g., ice cream) the weight ratio ranges from about 1:10 to about 1:20, about 1:13, about 1:16, or about 1:19. For yoghurt, the weight ratio ranges from about 1:8 to about 1:20, about 1:10, about 1:12, about 1:14, about 1:16, or about 1:18.

In another embodiment of the present invention, the 4-amino-5,6-dimethylthieno[2,3-d]pyrimidine-2(1H)-one is present as its hydrochloride salt. In another embodiment, composition comprises 4-amino-5,6-dimethylthieno[2,3-d] pyrimidine-2(1H)-one hydrochloride, sucralose and a carrier such as dextrose, lactose, maltodextrin or water.

One embodiment of the present invention provides a process of making a composition comprising solid particles of 4-amino-5,6-dimethylthieno[2,3-d]pyrimidine-2(1H)-one or salts, solvates, and/or esters thereof, and sucralose by a spray drying process. The term "spray-drying" broadly refers to processes involving breaking up liquid mixtures into small droplets (atomization) and rapidly removing solvent from the mixture in a spray-drying apparatus where there is a strong driving force for evaporation of solvent from the droplets. For example, 4-amino-5,6-dimethylthieno[2,3-d]pyrimidine-2 (1H)-one or salts, solvates, and/or esters thereof, and the sucralose are both dissolved or dispersed in a common solvent (e.g., water), and the resulting solution and or dispersion is spray dried. The resulting spray dried particles each comprise an intimate and essentially homogeneous blend of the 4-amino-5,6-dimethylthieno[2,3-d]pyrimidine-2(1H)-one or salts, solvates, and/or esters thereof and the sucralose. Solid particles of the claimed composition prepared by spray drying have different dissolution and stability properties compared to essentially the same composition prepared by other methods Solvents suitable for spray-drying can be any liquid in which each of 4-amino-5,6-dimethylthieno[2,3-d]pyrimidine-2(1H)-one or salts, solvates, and/or esters thereof and the sucralose are soluble and/or dispersed. Preferably, the solvent is also volatile with a boiling point of 150° C. or less. In addition, the solvent should have relatively low toxicity. In some embodiments, suitable spray drying solvents include water, alcohols such as methanol, ethanol, n-propanol, iso-propanol, and butanol; ketones such as acetone, methyl ethyl ketone and methyl iso-butyl ketone; esters such as ethyl acetate and propylacetate; and various other solvents such as acetonitrile, methylene chloride, toluene, and 1,1,1-trichloroethane. Lower volatility solvents such as dimethyl acetamide or dimethylsulfoxide can also be used. Mixtures of solvents, such as 50% methanol and 50% acetone, can also be used, as can mixtures with water, so long as the sucralose and 4-amino-5,6-dimethylthieno[2,3-d]pyrimidine-2(1H)-one or salts, solvates, and/or esters thereof are sufficiently soluble to make the spray-drying process practicable.

The strong driving force for solvent evaporation is generally provided by maintaining the partial pressure of solvent in the spray-drying apparatus well below the vapor pressure of the solvent at the temperature of the drying droplets. This is accomplished by (1) maintaining the pressure in the spray-drying apparatus at a partial vacuum (e.g., 0.01 to 0.50 atm); or (2) mixing the liquid droplets with a warm drying gas; or (3) both (1) and (2). In addition, a portion of the heat required for evaporation of solvent may be provided by heating the spray solution.

The relative proportion of each components namely, 4-amino-5,6-dimethylthieno[2,3-d]pyrimidine-2(1H)-one or salts, solvates, and/or esters thereof and at least one sweetener in the solid particle will depend on the ratio and solubilities of the two components in the solvent utilized for spray drying. In one embodiment the relative proportion ranges from about 0.002% to about 50% weight of the sweetener, and about 99.008% to about 50% weight of 4-amino-5,6-dimethylthieno[2,3-d]pyrimidine-2(1H)-one or salts, solvates, and/or esters thereof. In another embodiment the relative proportion ranges from about 20% to about 50% weight of the sweetener, and about 80% to about 50% weight of 4-amino-5,6-dimethylthieno[2,3-d]pyrimidine-2(1H)-one or salts, solvates, and/or esters thereof.

In one embodiment, a sweet taste modulating amount of the composition of the present invention is incorporated into food products or formulations optionally in the presence of known sweeteners. e.g., so that the sweet flavor modified food product has an increased sweet taste as compared to the food product without the sweet taste modulating amount of the composition, as judged by human beings or animals in general, or in the case of formulations testing, as judged by a majority of a panel of at least 3 human taste testers, via procedures commonly known in the field. In another embodiment, the compositions of the present invention can be formulated in flavor preparations to be added to food or products.

In other embodiments, the compositions of the present invention allow the amount of sucralose, e.g., in an ingestible compositions such as a food, to be reduced due the sweetness enhancing effects of the 4-amino-5,6-dimethylthieno[2,3-d] pyrimidine-2(1H)-one or salts, solvates, and/or esters thereof. The amount of reduction of the sucralose, relative to the amount of sucralose in the conventional sucralose-containing ingestible composition without 4-amino-5,6-dimethylthieno [2,3-d]pyrimidine-2(1H)-one or salts, solvates, and/or esters thereof, can be in the range of about 10 wt. % to about 90 wt. %, including reductions of about 15 wt. %, about 20 wt. %, about 25 wt. %, 30 about wt. %, about 35 wt. %, about 40 wt. %, about 45 wt. %, about 50 wt. %, about 55 wt. %, about 60 wt. %, about 65 wt. %, about 70 wt. %, about 75 wt. %, about 80 wt. %, or about 85 wt. %, inclusive of all ranges and subranges therebetween.

The amount of 4-amino-5,6-dimethylthieno[2,3-d]pyrimidine-2(1H)-one or salts, solvates, and/or esters thereof present in ingestible compositions having reduced levels of sucralose (as disclosed herein) can range from about 0.1 ppm to about 2000 ppm, including about 0.5 ppm, about 1 ppm, about 2 ppm, about 3 ppm, about 4 ppm, about 5 ppm, about 6 ppm, about 7 ppm, about 8 ppm, about 9 ppm, about 10 µm, about 15 ppm, about 20 ppm, about 25 ppm, about 30 ppm, about 35 ppm, about 40 ppm, about 50 ppm, about 60 ppm, about 70 ppm, about 80 ppm, about 90 ppm, about 100 ppm, about 150 ppm, about 200 ppm, about 250 ppm, about 300 ppm, about 350 ppm, about 400 ppm, about 500 ppm, about 600 ppm, about 700 ppm, about 800 ppm, about 900 ppm, about 1000 ppm, about 1200 ppm, about 1400 ppm, about 1600 ppm, about 1800 ppm, inclusive of all values, ranges and subranges therebetween.

Similarly, the compositions of the present invention can improve the sweetness delivery profile of sucralose-containing ingestible compositions.

When the sweetness or sweetness delivery profile characteristics of compositions containing sucralose are compared with compositions comprising combinations of sucralose and 4-amino-5,6-dimethylthieno[2,3-d]pyrimidine-2(1H)-one or salts, solvates and/or esters thereof, any conventional organoleptic techniques may be used as described herein, including paired comparison tests, difference testing, time intensity testing, descriptive analysis, etc. When compositions are deemed to have "substantially" the same sweetness or sweetness delivery profile, these characteristics are not readily distinguishable using conventional organoleptic techniques.

In another embodiment food products that comprise the compositions of the present invention are prepared by means of conventional mixing, dissolving, granulating the ingredients into various forms comprising solid, semi-solid, and liquid foods. Various additives may be mixed, ground, or granulated with the compositions of this invention to form suitable food materials. Compositions of the invention may be formulated into foods so that they are delivered as a dry powder or a liquid suspension. In one embodiment, the composition of the present invention is formulated as a liquid or as a paste at the time of preparation. In other embodiments the composition is formulated as a dry powder with a liquid, typically water, added at a later time but prior to mixing with the other food ingredients.

Thieno[2,3-d]pyrimidine derivatives including 4-amino-5, 6-dimethylthieno[2,3-d]pyrimidine-2(1H)-one can be prepared by synthetic methods known to one skilled in the art. In one embodiment, as illustrated in Scheme 1 below, thieno[2, 3-d]pyrimidine derivatives are prepared from 2-aminothiophene derivatives via the Gewald reaction (Chen et al., *Synthetic Communication* 2004, 34, 3801 and references cited therein; Elmegeed et al., *Eur. J. Med. Chem.* 2005, 40, 1283 and references cited therein). Additional details can be found in the International Application No. PCT/US2008/065650, filed Jun. 3, 2008 and entitled "Modulation of Chemosensory Receptors and Ligands Associated Therewith", the content of which is herein incorporated by reference in their entirety for all purposes. Thus, 2-aminothiophene derivatives are key intermediates for preparing thieno[2,3-d]pyrimidine derivatives including 4-amino-5,6-dimethylthieno[2,3-d]pyrimidine-2(1H)-one.

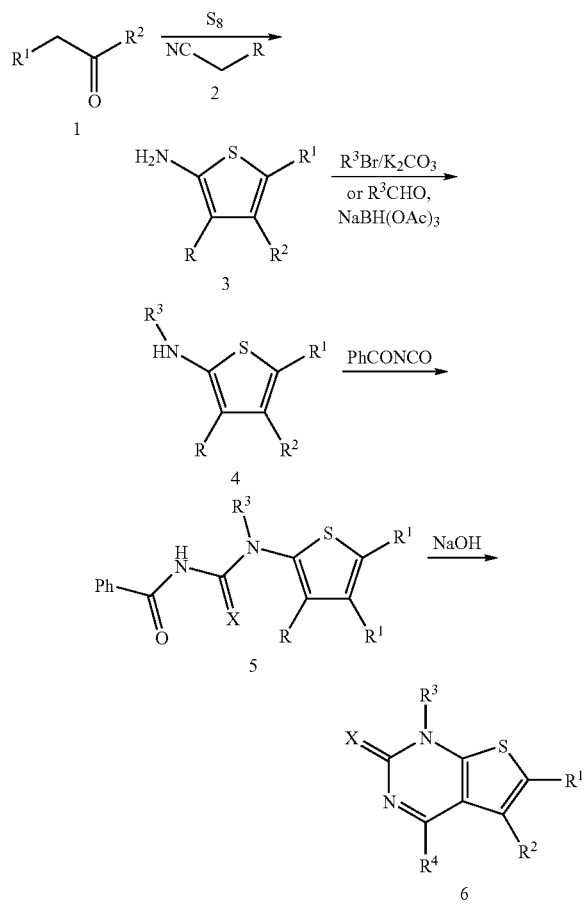

Scheme 1

R1 is hydrogen or alkyl;
R2 is hydrogen or alkyl;
R = CN, CO$_2$R$^4$, or COR$^4$;
R$^3$ is alkyl; and
R$^4$ is hydrogen or alkyl.

In one embodiment, the present invention provides a process of preparing a 2-aminothiophene derivative having structural Formula (a):

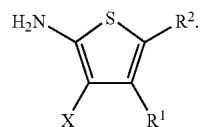

The process comprises mixing a compound having structural Formula (b):

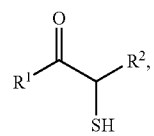

with a compound having structural Formula (c)

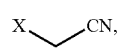

in the presence of an organic amine at a temperature of about 0° C. or below to obtain a reaction mixture; maintaining the reaction mixture at a temperature of about 0° C. or below for about 30 to about 90 minutes; concentrating the reaction mixture to obtain a slurry; and filtering the slurry to obtain the compound having structural Formula (a) as solid particles; wherein: R$^1$ is hydrogen, alkyl, heteroalkyl, aryl, heteroaryl, arylalkyl, or heteroarylalkyl; R$^2$ is hydrogen, alkyl, heteroalkyl, alkenyl, aryl, heteroaryl, arylalkyl, or heteroarylalkyl; or alternatively, R$^1$ and R$^2$, together with the atoms to which they are attached, form a carbocyclic ring or heterocyclic ring; X is CN or —C(O)R$^3$; R$^3$ is alkyl, aryl, heteroaryl, arylalkyl, heteroarylalkyl, OR$^4$, or N(R$^4$)$_2$; and each R$^4$ is independently hydrogen, alkyl, aryl, heteroaryl, arylalkyl, or heteroarylalkyl. In one embodiment of the present process, R$^1$ is hydrogen or alkyl; R$^2$ is hydrogen or alkyl; and X is CN. In another embodiment of the present process, R$^1$ is methyl; R$^2$ is methyl; and X is CN.

In one embodiment, the mixing step comprises mixing a solution of the compound having structural Formula (b) with a solution of the compound having structural Formula (c) in the presence of an organic amine. Each of the solutions can have the same or different solvent. In one embodiment, each of the solutions can have the same or different alcohol solvent. In one embodiment of the present process, the mixing step comprises adding an alcohol solution of the compound having structural Formula (b) to an alcohol solution of the compound having structural Formula (c) and the organic amine at a temperature of about 0° C. or below. The temperature is maintained at about 0° C. or below throughout the adding step. Thus, the adding process needs to be controlled at such a rate that the temperature of the resulting reaction mixture dose not arise to above 0° C. Depending on the amount of material and the means of controlling temperature, the duration of the adding step varies substantially. The an alcohol solution of the compound having structural Formula (c) and the organic amine can be prepared by mixing the compound having structural Formula (c) and the organic amine in an alcohol solvent at a temperature of about 10° C.

or below with the temperature of about 5° C. or below more preferred. The alcohol can be methanol, ethanol, n-propanol, isopropanol, or a combination thereof.

In one embodiment, the reaction mixture is maintained at a temperature of about 0° C. or below for about 45 to about 75 minutes. In another embodiment, the reaction mixture is maintained at a temperature of about 0° C. or below for about 60 minutes. In one embodiment, the temperature for the mixing step is from about −20° C. to about 0° C. In another embodiment, the temperature for the mixing step is from about −15° C. to about 0° C. In another embodiment, the temperature for the mixing step is from about −10° C. to about −5° C. In one embodiment, the temperature for the maintaining step is from about −20° C. to about 0° C. In another embodiment, the temperature for the maintaining step is from about −15° C. to about 0° C. In another embodiment, the temperature for the maintaining step is from about −10° C. to about −5° C.

In one embodiment of the present process, the reaction mixture is concentrated by evaporating the solvent. The evaporation can be accomplished by any means known to one skilled in the art including, but are not limited to applying vacuum to the reaction mixture, elevating temperature of the reaction mixture, spinning the reaction mixture on a solid surface, stirring the reaction mixture, blowing air or other gas to the surface of the reaction mixture, and any combination thereof. Preferably, the temperature of the reaction mixture during the evaporation process is not higher than about 50° C. In one embodiment, the evaporation is accomplished by rotovaping the reaction mixture at a temperature of about 50° C. or below with the temperature of about 40° C. or below more preferred.

In one embodiment, the concentration step comprises reducing the volume of the reaction mixture to about 60% or less of its original volume. In another embodiment, the concentration step comprises reducing the volume of the reaction mixture to about 50% or less of its original volume. In another embodiment, the concentration step comprises reducing the volume of the reaction mixture to about 40% or less of its original volume. In another embodiment, the concentration step comprises reducing the volume of the reaction mixture to about 30% or less of its original volume. In yet another embodiment, the concentration step comprises evaporating all or most of the solvent to obtain a dried or semi-dried reaction mixture and re-adding the solvent to the dried or semi-dried reaction mixture to obtain a slurry. The amount of the re-added solvent can be from about 30% to about 60% of the original amount.

In one embodiment, the filtrate of the filtering step, i.e., the solvent passing through the filter, can be concentrated to obtain a slurry according to the procedure described above. The slurry can be filtered to obtain the compound having structural Formula (a) as solid particles.

In one embodiment of the present process, the molar ratio of the compound having structural formula (b) to the compound having structural formula (c) is from about 1:0.9 to about 1:1.1. In another embodiment of the present process, the molar ratio of the compound having structural formula (b) to the compound having structural formula (c) is about 1:1. In one embodiment of the present process, the molar ratio of the compound having structural formula (c) to the organic amine is from about 5.1:1 to about 4.9:1. In another embodiment of the present process, the molar ratio of the compound having structural formula (c) to the organic amine is about 5:1.

In one embodiment, the process described above further comprises washing the solid particles of the compound having structural Formula (a) with an eluting solvent, wherein the eluting solvent is a mixture of an alcohol solvent and an alkane hydrocarbon solvent. In one embodiment, the volume ratio of the alcohol solvent to the alkane hydrocarbon solvent is from about 1:9 to about 1:2. In another embodiment, the volume ratio of the alcohol solvent to the alkane hydrocarbon solvent is from about 1:7 to about 1:3. In another embodiment, the volume ratio of the alcohol solvent to the alkane hydrocarbon solvent is about 1:4.

The above-described process provides a manufacturable process for the preparation of 2-aminothiophene derivatives including 2-amino-3-cyano-4,5-dimethylthiophene. By "manufacturable process", it is meant a large scale process suitable for industrial production. Specifically, the present process involves short reaction times thereby minimizing time spent in the plant and reducing plant costs. The process also provides a highly pure solid material that is easy to handle. For example, as described hereinbelow in Example 13, the 2-aminothiophene product can be obtained after a simple wash protocol with greater than 99% purity by HPLC. That is, the present invention provides a process of preparing 2-aminothiophene that does not comprise chromatographic purification. The reaction yield is mostly from about 60 to about 70%. Furthermore, the reaction can be run at higher concentrations thereby reducing solvent costs and being more environmentally friendly.

The term "alkyl" herein means a saturated branched, straight-chain or cyclic organic radical derived by the removal of one hydrogen atom from a single carbon atom of a parent alkane. The term "alkyl" includes cycloalkyl. In one embodiment of the present invention, the alkyl group contains from 1 to 12 carbon atoms ($C_1$-$C_{12}$ alkyl). In another embodiment of the present invention, the alkyl group contains from 1 to 6 carbon atoms ($C_1$-$C_6$ alkyl). Examples of alkyl groups include, but are not limited to, methyl; ethyl; propyls such as propan-1-yl, propan-2-yl (isopropyl), cyclopropan-1-yl, etc.; butyls such as butan-1-yl, butan-2-yl (sec-butyl), 2-methyl-propan-1-yl (isobutyl), 2-methyl-propan-2-yl (1-butyl), cyclobutan-1-yl, etc.; cyclopropyl, cyclobutyl, cyclopentyl, and the like. The alkyl group may be further optionally substituted.

The term "alkenyl" herein means an unsaturated branched, straight-chain or cyclic organic radical having at least one carbon-carbon double bond derived by the removal of one hydrogen atom from a single carbon atom of a parent alkene. The term "alkenyl" includes cycloalkenyl. The group may be in either the cis or trans conformation about the double bond(s). In one embodiment of the present invention, the alkenyl group contains from 2 to 14 carbon atoms ($C_2$-$C_{14}$ alkyl). In another embodiment of the present invention, the alkenyl group contains from 2 to 8 carbon atoms ($C_2$-$C_8$ alkyl). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. The alkenyl group may be further optionally substituted.

The term "aryl" herein means a monovalent aromatic hydrocarbon group derived by the removal of one hydrogen atom from a single carbon atom of a parent aromatic ring system, as defined herein. Examples of aryl group include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl). In other embodiments, an aryl group comprises from 6 to 15 carbon atoms ($C_6$-$C_{15}$ aryl). In still other embodiments, an aryl group comprises from 6 to 15 carbon atoms ($C_6$-$C_{10}$ aryl). The aryl group may be further optionally substituted.

The term "heteroaryl" herein means a monovalent heteroaromatic radical derived by the removal of one hydrogen atom from a single atom of a parent heteroaromatic ring systems, as defined herein. Examples of heteroaryl group include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine. The heteroaryl group may be further optionally substituted.

The term "heteroalkyl" herein means an alkyl group, respectively, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl group. The heteroalkyl group may be further optionally substituted.

The term "arylalkyl" herein means an alkyl group in which one of the hydrogen atoms bonded to a carbon atom, typically a terminal or $sp^3$ carbon atom, is replaced with an aryl group as, as defined herein. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. In some embodiments, an arylalkyl group is ($C_6$-$C_{30}$) arylalkyl, e.g., the alkyl moiety of the arylalkyl group is ($C_1$-$C_{10}$) alkyl and the aryl moiety is ($C_6$-$C_{20}$) aryl. In other embodiments, an arylalkyl group is ($C_6$-$C_{20}$) arylalkyl, e.g., the alkyl moiety of the arylalkyl group is ($C_1$-$C_8$) alkyl and the aryl moiety is ($C_6$-$C_{12}$) aryl. In still other embodiments, an arylalkyl group is ($C_6$-$C_{15}$) arylalkyl, e.g., the alkyl moiety of the arylalkyl group is ($C_1$-$C_5$) alkyl and the aryl moiety is ($C_6$-$C_{10}$) aryl. The arylalkyl group may be further optionally substituted.

The term "heteroarylalkyl" herein means an alkyl group in which one of the hydrogen atoms bonded to a carbon atom, typically a terminal or $sp^3$ carbon atom, is replaced with a heteroaryl group. In some embodiments, the heteroarylalkyl group is a 6-21 membered heteroarylalkyl, e.g., the alkyl moiety of the heteroarylalkyl is ($C_1$-$C_6$) alkyl and the heteroaryl moiety is a 5-15-membered heteroaryl. In other embodiments, the heteroarylalkyl is a 6-13 membered heteroarylalkyl, e.g., the alkyl moiety is ($C_1$-$C_3$) alkyl and the heteroaryl moiety is a 5-10 membered heteroaryl. The heteroarylalkyl group may be further optionally substituted.

The term "carbocyclic" herein means a saturated or unsaturated cyclic alkyl or alkenyl radical. Examples of carbocyclic group include, but are not limited to, groups derived from cyclopropane, cyclobutane, cyclopentane, cyclohexane, and the like. In some embodiments, a carbocyclic group comprises from 3 to 10 ring atoms ($C_3$-$C_{10}$ cycloalkyl). In other embodiments, a carbocyclic group comprises from 3 to 7 ring atoms ($C_3$-$C_7$ cycloalkyl). The carbocyclic group may be further optionally substituted.

The term "heterocyclic" herein means a saturated or unsaturated cyclic alkyl or alkenyl radical in which one or more carbon atoms (and optionally any associated hydrogen atoms) are independently replaced with the same or different heteroatom. Typical heteroatoms to replace the carbon atom(s) include, but are not limited to, B, N, P, O, S, Si, etc. Examples of heterocyclic group include, but are not limited to, groups derived from epoxides, azirines, thiiranes, imidazolidine, morpholine, piperazine, piperidine, pyrazolidine, pyrrolidone, quinuclidine, borolane, dioxaborolane, and the like. In some embodiments, the heterocyclic group comprises from 3 to 10 ring atoms (3-10 membered heterocyclic). In other embodiments, the heterocyclic group comprise from 5 to 7 ring atoms (5-7 membered heterocyclic). A heterocyclic group may be substituted at a heteroatom, for example, a nitrogen atom, with a ($C_1$-$C_6$) alkyl group. As specific examples, N-methyl-imidazolidinyl, N-methyl-morpholinyl, N-methyl-piperazinyl, N-methyl-piperidinyl, N-methyl-pyrazolidinyl and N-methyl-pyrrolidinyl are included within the definition of "heterocyclic." A heterocyclic group may be attached to the remainder of the molecule via a ring carbon atom or a ring heteroatom. The heterocyclic group may be further optionally substituted.

The term "alcohol" herein means an organic compound in which a hydroxyl group (—OH) is bound to a carbon atom of an alkyl or substituted alkyl group. The alcohol includes primary, secondary, and tertiary alcohols. Examples of alcohol include, but are not limited to, methanol, ethanol, n-propanol, isopropanol, n-butanol, s-butanol, and t-butanol. The alcohol may be further optionally substituted.

The term "alkane hydrocarbon" herein means an organic compound or a mixture of organic compounds which consist of hydrogen and carbon and contain no or trace amount of unsaturated carbon-carbon bond. Examples of alkane hydrocarbon include, but are not limited to, hexanes and heptanes.

The term "organic amine" herein denotes a compound having structural formula $N(R)_3$, wherein each R is independently hydrogen, alkyl, alkenyl, aryl, heteroaryl, heteroalkyl, arylalkyl, or heteroarylalkyl, or alternatively, two of R, together with the nitrogen atom to which they are attached, form a heterocyclic ring. Examples of organic amine include, but are not limited to, methylamine, dimethylamine, diethylamine, methylethylamine, triethylamine, diisopropylethylamine (DIEA), morpholine, piperidine, and combinations thereof.

The term "substituted", when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =$O$, —$OR^b$, —$SR^b$, —$S^-$, =$S$, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2O^-$, —$S(O)_2OR^b$, —$OS(O)_2R^b$, —$OS(O)_2O^-$, —$OS(O)_2OR^b$, —$P(O)(O^-)$, —$P(O)(OR^b)(O^-)$, $P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, substituted alkyl, arylalkyl, alkyldiyl, substituted alkyldiyl, aryl, substituted aryl, arylalkyl, substituted arylalkyl, heteroalkyl, substituted heteroalkyl, heteroalkyldiyl, substituted heteroalkyldiyl, heteroaryl, substituted heteroaryl, heteroarylalkyl substituted heteroarylalkyl; each $R^b$ is independently hydrogen or $R^a$; and each $R^c$ is independently $R^b$ or alternatively, the two $R^c$ are taken together with the nitrogen atom to which they are bonded form a cycloheteroalkyl ring which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl.

EXAMPLES

The term "Compound A" as used hereinblow refers to "4-amino-5,6-dimethylthieno[2,3-d]pyrimidine-2(1H)-one" or "4-amino-5,6-dimethylthieno[2,3-d]pyrimidine-2(1H)-one hydrochloride".

Example 1

General Procedure for Preparation of Spray Dried Solid Particles

Solid particles were prepared using a spray-drying apparatus. 4-Amino-5,6-dimethylthieno[2,3-d]pyrimidine-2 (1H)-one hydrochloride, and sucralose were mixed in a solvent (water) together with maltodextrin to form a spray solution. A Buchi lab spray dryer model # B-290 was utilized for the lab formulation and procedure work for spray drying. Solid particles comprising the composition of the invention were prepared according to the spray dried formulation in Table I.

The solid particles were prepared according to the following procedure:
Water was pre-weighed in a beaker and each of Star-Dri 10 Maltodextrin, Sucralose and 4-amino-5,6-dimethylthieno[2,3-d]pyrimidine-2(1H)-one hydrochloride (100× in PG) were pre-weighted and set aside separately. The water beaker was placed on a heat plate equipped with a stirring bar and the stir knob (700-800 rpm) turned on to create a vortex in the water beaker. The maltodextrin was added with stirring until all the maltodextrin dissolved. Sucralose and COMPOUND A (3% in PG) were added and the stirring continued until all ingredients dissolved. The solution was then spray dried using a Buchi mini spray dryer with specifications of inlet temperature=155-160° C., outlet temperature=100° C. and Pump %=30. The brix of the solution is 42.1

TABLE I

| Ingredient | Percentage | Actual weight (grams) | Percent of Dry (wt/wt) |
|---|---|---|---|
| Star-Dri 10 Maltodextrin | 38.30400 | 38.3040 | 95.76000 |
| Sucralose | 1.60000 | 1.60000 | 4.00000 |
| 4-amino-5,6-dimethylthieno [2,3-d]pyrimidine-2(1H)-one hydrochloride (3% in propylene glycol) | 3.20000 | 3.2000 | 0.24000 |
| Water | 56.89600 | 56089600 | 0.00000 |
| Total | 100.00000 | 100.00000 | 100.0000 |

Example 2

For comparison purposes, dry blends of 4-amino-5,6-dimethylthieno[2,3-d]pyrimidine -2(1H)-one hydrochloride and sucralose were made to demonstrate that solid particles with uniform ratios of dimethylthieno[2,3-d]pyrimidine-2(1H)-thione hydrochloride:sweetener were not obtained, as determined by HPLC.

Example 3

For comparison of dissolution rates, sucralose (Splenda®), dry blends of 4-amino-5,6-dimethylthieno[2,3-d]pyrimidine-2(1H)-one hydrochloride and sucralose, and spray dried particles comprising 4-amino-5,6-dimethylthieno[2,3-d]pyrimidine-2(1H)-one and sucralose were dissolved in beverage or liquid, and the time taken for each composition to go into solution was measured visually. Table II gives the dissolution rates. The net weight of each of the sucralose, the dry blended 4-amino-5,6-dimethylthieno[2,3-d]pyrimidine-2(1H)-one hydrochloride and sucralose, and spray dried particles comprising 4-amino-5,6-dimethylthieno[2,3-d]pyrimidine-2 (1H)-one and sucralose, and spray dried 4-amino-5,6-dimethylthieno[2,3-d]pyrimidine-2(1H)-one hydrochloride and sucralose, and spray dried particles comprising 4-amino-5,6-dimethylthieno[2,3-d]pyrimidine-2(1H)-one and sucralose in duplicate runs was 1.00 g. The volume of tested beverage or liquid was 120 mL. 1.00 g of each composition was dissolved into 120 mL of test liquid, using a 1" stir bar over a magnetic stirrer (model # Fisher Scientific Isotemp) at 600-700 rpms

TABLE II

| Ingredients | Water 20° | Cold Water 5° | Hot Water 66° C. | Ice Tea 5° C. | Hot Coffee 66° C. |
|---|---|---|---|---|---|
| Splenda Packet | 40 seconds | 1 minute, 8 seconds | 5 seconds | 1 minute, 52 seconds | 15 seconds |

TABLE II-continued

| Ingredients | Water 20° | Cold Water 5° | Hot Water 66° C. | Ice Tea 5° C. | Hot Coffee 66° C. |
|---|---|---|---|---|---|
| dry blended 4-amino-5,6-dimethylthieno[2,3-d]pyrimidine-2(1H)-one hydrochloride and sucralose, in duplicate | >5 minutes | >5 minutes | 1 minute, 50 seconds | >5 minutes | 3 minutes, 25 seconds |
| Spray Dried 4-amino-5,6-dimethylthieno[2,3-d]pyrimidine-2(1H)-one hydrochloride and sucralose, in duplicate | 35 seconds | 1 minute, 2 seconds | 5 seconds | 1 minutes, 57 seconds | 25 seconds |

Example 4

Hot Cocoa

Hot cocoa compositions were prepared using the following ingredients and evaluated for sweetness and/or lingering taste. Formulation (b) comprising reduced sucralose and 10 ppm of 4-amino-5,6-dimethylthieno[2,3-d]pyrimidine-2(1H)-one had approximately the same sweetness as formulation (a) which comprised 100% sucralose.

TABLE III

| Ingredients | Sample weight (grams) 100% sucralose hot cocoa (a) | Sample weight (grams) Reduced sucralose hot cocoa (b) |
|---|---|---|
| Instant non fat dry milk Fortified with Vitamin A &D, Kroger | 6.00 | 6.00 |
| Quality Ingredients, Creamer #4403 | 4.00 | 4.00 |
| Alto cocoa, Guittard | 4.00 | 4.00 |
| Kel Cam 280, CP Kelco | 0.060 | 0.060 |
| Vanilla Flavor | 0.10 | 0.100 |
| Salt | 0.200 | 0.200 |
| Sucralose | 0.0350 | 0.0176 |
| Maltodextrin | 5.605 | 5.4224 |
| 4-amino-5,6-dimethylthieno[2,3-d]pyrimidine-2(1H)-one 0.1% in Propylene Glycol | 0 | 0.2000 (10 ppm neat) |
| Total Weight | 20.000 | 20.000 |

The hot cocoa powder is reconstituted with 6 fl. oz. hot water (20 g powder+approximately 180 g hot water); 4-amino-5,6-dimethylthieno[2,3-d]pyrimidine-2(1H)-one will be approximately 1 ppm as consumed.

Human Taste Test:

Paired comparison taste test with Hot Cocoa with 175 ppm Sucralose vs. Hot Cocoa with 87.5 ppm Sucralose. Panelists evaluate two hot cocoa samples in a paired comparison taste test procedure and are instructed to select the sweeter of the two samples. They perform a total of three paired comparison tests each containing the following samples: Hot Cocoa with 175 ppm Sucralose vs. Hot Cocoa with 87.5 ppm Sucralose.

Conclusions:

Panelists found Hot Cocoa with 175 ppm Sucralose was significantly sweeter than Hot Cocoa with 87.5 ppm Sucralose ($p<0.05$). 42 of 45 tests indicated Hot Cocoa with 175 ppm Sucralose was the sweeter sample.

TABLE IV

Sample selected as sweeter by panelists Hot Cocoa with 175 ppm Sucralose vs. Hot Cocoa with 87.5 ppm Sucralose. n = 45 (15 panelists × 3 reps).

| Samples | Test 1 | Test 2 | Test 3 | Total |
|---|---|---|---|---|
| Hot Cocoa with 175 ppm Sucralose | 13 | 14 | 15 | 42 |
| Hot Cocoa with 87.5 ppm Sucralose | 2 | 1 | 0 | 3 |
| Total | 15 | 15 | 15 | 45 |
| Hot Cocoa with 175 ppm Sucralose selected (p-value) | 0.004 | <0.004 | <0.004 | <0.001 |

Human Taste Test:

Paired comparison taste test with Hot Cocoa with 175 ppm Sucralose vs. Hot Cocoa with 87.5 ppm Sucralose+10 ppm Compound A. Panelists evaluate two hot cocoa samples in a paired comparison taste test procedure and are instructed to select the sweeter of the two samples. They perform a total of three paired comparison tests each containing the following samples: Hot Cocoa with 175 ppm Sucralose vs. Hot Cocoa with 87.5 ppm Sucralose+10 ppm Compound A.

Conclusions:

Panelists found Hot Cocoa with 175 ppm Sucralose was not significantly different than Hot Cocoa with 87.5 ppm Sucralose+10 ppm Compound A ($p<0.10$). 26 of 45 tests indicated Hot Cocoa with 87.5 ppm Sucralose+10 ppm Compound A was the sweeter sample.

TABLE V

Sample selected as sweeter by panelists Hot Cocoa with 175 ppm Sucralose vs. Hot Cocoa with 87.5 ppm Sucralose + 10 ppm Compound A. n = 45 (15 panelists × 3 reps).

| Samples | Test 1 | Test 2 | Test 3 | Total |
|---|---|---|---|---|
| Hot Cocoa with 175 ppm Sucralose | 8 | 6 | 5 | 19 |
| Hot Cocoa with 87.5 ppm Sucralose | 7 | 9 | 10 | 26 |
| Total | 15 | 15 | 15 | 45 |
| Hot Cocoa with 175 ppm Sucralose selected (p-value) | >0.774 | 0.607 | 0.302 | 0.371 |

Example 5

Pudding

Pudding compositions were prepared using the following ingredients and evaluated for sweetness and/or lingering taste. Composition (e) comprising 50% sucralose and 8:5 ppm of 4-amino-5,6-dimethylthieno[2,3-d]pyrimidine-2(1H)-one had approximately the same sweetness as composition (c) which comprised 100% sucralose. Composition (d) comprising 50% sucralose and 7.5 ppm of 4-amino-5,6-dimethylthieno[2,3-d]pyrimidine-2(1H)-one was not as sweet as composition (c) which comprised 100% sucralose.

TABLE VI

| Ingredients | Sample weight (grams) 100% sucralose pudding (c) | Sample weight (grams) 50% sucralose pudding (d) | Sample weight (grams) 50% sucralose pudding (e) |
|---|---|---|---|
| Albertson's Lowfat milk Vitamin A & D, 1% Milk Fat | 60.0 | 60.0 | 60.0 |
| National 465 Food Starch Modified | 5.0 | 5.0 | 5.0 |
| Jerzee Blend TUF-1HD 175545, Diehl | 1.5 | 1.5 | 1.5 |
| Salt | 0.25 | 0.25 | 0.25 |
| Pure Vanilla Extract, Kroger | 0.5 | 0.5 | 0.5 |
| Sucralose | 0.0250 (250 ppm) | 0.0125 (125 ppm) | 0.0125 (125 ppm) |
| Color yellow #5 | 0.00150 | 0.00150 | 0.00150 |
| Water | 32.7235 | 31.986 | 31.8860 |
| 4-amino-5,6-dimethylthieno[2,3-d]pyrimidine-2(1H)-one* 0.1% in Propylene Glycol | 0 | 0.75 (7.5 ppm neat) | 0.85 (8.5 ppm neat) |
| Total Weight | 100.00 | 100.00 | 100.00 |

*4-amino-5,6-dimethylthieno[2,3-d]pyrimidine-2(1H)-one will be approximately 7.5-8.5 ppm as consumed (100 g cup of pudding).

30 panelists evaluated compositions (c) and (e) in a paired comparison taste test. The panelists were asked to pick the sweeter of the two samples. All the samples were completely randomized. Twenty-one of the thirty panelists rated composition (e) as sweeter than composition (c) as shown in Table V.

TABLE VII

Results of the paired comparison test: 100% sucralose versus 50% sucralose + 8.5 ppm 4-amino-5,6-dimethylthieno[2,3-d]pyrimidine-2(1H)-one vanilla pudding, n = 30 (10 panelists × 3 rep.)

| Samples | All Tests 1 vs 2 | All Tests 3 vs 4 | All Tests 5 vs 6 | Totals |
|---|---|---|---|---|
| 100% sucralose vanilla pudding | 5 | 2 | 2 | 9 |
| 50% sucralose + 8.5 ppm of Compound A vanilla pudding | 5 | 8 | 8 | 21 |
| Total | 10 | 10 | 10 | 30 |

Example 6

Cookies

Cookies were prepared using the following ingredients and evaluated for sweetness and/or lingering taste. Composition (g) comprising 100 ppm of sucralose and 22 ppm of 4-amino-5,6-dimethylthieno[2,3-d]pyrimidine-2(1H)-one had approximately the same sweetness as composition (f) which comprised 100% sucralose. (200 ppm of sucralose).

TABLE VIII

| Ingredients | Sample weight (grams) 100% sucralose cookies (f) | Sample weight (grams) 50% reduced sucralose cookies (g) |
|---|---|---|
| Flour | 205.3 | 205.3 |
| Baking soda | 2.5 | 2.5 |
| Butter, Salted | 0.5 | 0.5 |
| Butter | 125.05 | 125.05 |
| Egg | 20.02 | 20.02 |
| Vanilla | 2.5 | 2.5 |
| Sucralose | 0.09 (200 ppm) | 0.045 (100 ppm) |
| Sugar | 74.84 | 74.84 |
| Water | 15 | 15 |
| Compound A (1% in Propylene Glycol) | 0 | 0.983 (22 ppm neat) |
| Total Weight | 445.8 | 446.74 |

4-amino-5,6-dimethylthieno[2,3-d]pyrimidine-2(1H)-one will be approximately 15 ppm as consumed (30 gram cookie).

Human Taste Test:

Paired comparison taste test with 100 ppm Sucralose Sugar Cookie+22 ppm Compound A vs. 200 ppm Sucralose Sugar Cookie.

Procedure:

Panelists evaluate two cookies in a paired comparison taste test procedure and are instructed to select the sweeter of the two samples. They perform a total of three paired comparison tests each containing the following samples: 100 ppm Sucralose Sugar Cookie+22 ppm Compound A vs. 200 ppm Sucralose Sugar Cookie.

Products:

Sugar Cookie=flour, baking soda, salt, butter, egg, vanilla, sugar, water, sucralose, and optionally Compound A Conclusions:

Panelists found the 200 ppm Sucralose Sugar Cookie was not significantly different in sweetness than the "100 ppm Sucralose Sugar Cookie+22 ppm Compound A" (p>0.10). 23 of 42 tests indicated 200 ppm Sucralose Sugar Cookie was the sweeter sample.

1/14 panelists chose the 200 ppm Sucralose Sugar Cookie as the sweeter sample in all three paired comparisons. 8/14 panelists chose the 200 ppm Sucrulose Sugar Cookie as the sweeter sample in two paired comparison tests. 4114 panelists chose the 200 ppm Sucralose Sugar Cookies as the sweeter sample in one paired comparison test. 1/14 panelists chose the 200 ppm Sucralose as the sweeter sample in zero paired comparison tests.

TABLE IX

Sample selected as sweeter by panelists: 200 ppm Sucralose Sugar Cookie vs. 100 ppm Sucralose Sugar Cookie + 22 ppm Compound A. n = 42 (14 panelists × 3 reps).

| Samples | Test 1 | Test 2 | Test 3 | Total |
|---|---|---|---|---|
| 200 ppm Sucralose Sugar Cookie | 6 | 9 | 8 | 23 |
| 100 ppm Sucralose Sugar Cookie + 22 ppm Compound A | 8 | 5 | 6 | 19 |
| Total | 14 | 14 | 14 | 42 |
| 200 ppm Sucralose Sugar Cookie selected (p-value) | >0.791 | 0.424 | 0.791 | 0.644 |

Example 7

Cola-Soda

Cola-soda was prepared using the following ingredients and evaluated for sweetness and/or lingering taste. Composition (i) comprising 50% sucralose and 12 ppm of 4-amino-5,6-dimethylthieno[2,3-d]pyrimidine-2(1H)-one hydrochloride had approximately the same sweetness as composition (h) which comprised 100% sucralose.

TABLE X

| Ingredients | Sample weight (grams) 100% sucralose cola-soda (h) | Sample weight (grams) 50% sucralose cola-soda (i) |
|---|---|---|
| Cola Emulsion | 0.45 | 0.45 |
| Phosphonic acid 50%, Astaris | 0.40 | 0.40 |
| Ace-K, Nutrinova | 0.0025 | 0.00 |
| Caramel color #105, DD Williamson | 0.150 | 0.150 |
| Caramel color #050, DD Williamson | 0.05 | 0.05 |
| Sucralose | 0.02 | 0.01 |
| Carbonated water | 98.8075 | 98.82 |
| Propylene Glycol | 0.12 | 0 |
| 4-amino-5,6-dimethylthieno[2,3-d]pyrimidine-2(1H)-one hydrochloride (1% in propylene glycol) | 0 ppm | 0.12 (12 ppm neat) |
| Total Weight | 100.0000 | 100.0000 |

Human Taste Tests:

Cola Paired Comparison of Cola+200 ppm Sucralose+25 ppm Acesulfame Potassium vs. Cola+100 ppm Sucralose Procedure:

Panelists evaluated two sweet solutions in a paired comparison taste test procedure and were instructed to select the sweeter of the two samples. Panelists performed a total of three paired comparison tests each containing the following samples: Cola+200 ppm Sucralose+25 ppm Acesulfame Potassium vs. Cola+100 ppm Sucralose.

Products:

Cola+Sucralose=caramel color 105, caramel color 050, sucralose, acesulfame K, cola emulsion E, phosphoric acid, propylene glycol, carbonated water.

Conclusions:

Panelists found that the Cola+200 ppm Sucralose+25 ppm Acesulfame Potassium sample was significantly sweeter than Cola+100 ppm Sucralose (p<0.05). 31 of 34 tests indicated Cola+200 ppm Sucralose+25 ppm Acesulfame Potassium was the sweeter sample; panelists could discriminate the sweetness difference between the two samples.

TABLE XI

Sample selected as sweeter by panelists Cola + 200 ppm Sucralose vs. Cola + 100 ppm Sucralose. n = 34 (17 panelists × 2 reps).

| Samples | Test 1 | Test 2 | Total |
|---|---|---|---|
| Cola + 200 ppm Sucralose + 25 ppm Acesulfame Potassium | 14 | 17 | 31 |
| Cola + 100 ppm Sucralose | 3 | 0 | 3 |
| Total | 17 | 17 | 34 |
| Cola + 200 ppm Sucralose selected (p-value) | 0.006 | <0.001 | <0.001 |

Cola Paired Comparison

Cola+200 ppm Sucralose+25 ppm Acesulfame Potassium vs. Cola+100 ppm Sucralose+12 ppm 4-amino-5,6-dimethylthieno[2,3-d]pyrimidine-2(1H)-one hydrochloride Procedure:

Panelists evaluated two sweet solutions in a paired comparison taste test procedure and were instructed to select the sweeter of the two samples. They performed a total of three paired comparison tests each containing the following samples: Cola+200 ppm Sucralose+25 ppm Acesulfame Potassium vs. Cola+100 ppm Sucralose+12 ppm 4-amino-5,6-dimethylthieno[2,3-d]pyrimidine-2(1H)-one hydrochloride.

Products:

Cola+Sucralose=caramel color 105, caramel color 050, sucralose, acesulfame K, cola emulsion E, phosphoric acid, propylene glycol, carbonated water, 4-amino-5,6-dimethylthieno[2,3-d]pyrimidine-2(1H)-one hydrochloride.

Conclusions:

Panelists found that Cola+200 ppm Sucralose+25 ppm Acesulfame Potassium was not significantly different in sweetness than Cola+100 ppm Sucralose+12 ppm 4-amino-5,6-dimethylthieno[2,3-d]pyrimidine-2(1H)-one hydrochloride (p>0.1). 18 of 34 tests indicated that Cola+200 ppm Sucralose+12 ppm 4-amino-5,6-dimethylthieno[2,3-d]pyrimidine-2(1H)-one hydrochloride was the sweeter sample; panelists could not discriminate the sweetness difference between the two samples. The removal of Acesulfame Potassium also reduces or eliminates the bitter or off taste from the drink.

TABLE XII

Sample selected as sweeter by panelists Cola + 200 ppm Sucralose + 25 ppm Acesulfame Potassium vs. Cola + 100 ppm Sucralose + 12 ppm 4-amino-5,6-dimethylthieno[2,3-d]pyrimidine-2(1H)-one hydrochloride. n = 34 (17 panelists × 2 reps).

| Samples | Test 1 | Test 2 | Total |
|---|---|---|---|
| Cola + 200 ppm Sucralose + 25 ppm Acesulfame Potassium | 8 | 8 | 16 |
| Cola + 100 ppm Sucralose + 12 ppm 4-amino-5,6-dimethylthieno[2,3-d]pyrimidine-2(1H)-one hydrochloride | 9 | 9 | 18 |
| Total | 17 | 17 | 34 |
| Cola + 200 ppm Sucralose selected (p-value) | >0.791 | >0.791 | 0.864 |

Example 8

Strawberry Flavored Water

Strawberry flavored beverage was prepared using the following ingredients and evaluated for sweetness and/or lingering taste. Composition (k) comprising 50% sucralose and 6.8 ppm of 4-amino-5,6-dimethylthieno[2,3-d]pyrimidine-2(1H)-one hydrochloride had approximately the same sweetness as composition (j) which comprised 100% sucralose.

TABLE XIII

| Ingredients | Sample weight (grams) 100% sucralose strawberry flavored water (j) | Sample weight (grams) 50% sucralose strawberry flavored water (k) |
|---|---|---|
| Nutriose FB 06 wheat dextrine-soluble fiber | 2.3800 | 2.3800 |
| Malic Acid | 0.0450 | 0.0450 |
| Strawberry flavor | 0.3000 | 0.3000 |
| Sucralose | 0.0100 | 0.0050 |
| Water | 97.1558 | 97.1620 |
| Ace K | 0.0012 | 0.0000 |
| Propylene glycol | 0.0680 | 0.0000 |
| Salt | 0.0400 | 0.0400 |
| Compound A (1% in Propylene Glycol) | 0.0000 | 0.0680 (6.8 ppm neat) |
| Total Weight | 100.0000 | 100.00 |

4-amino-5,6-dimethylthieno[2,3-d]pyrimidine-2(1H)-one will be approximately 20.4 ppm as consumed (12 oz beverage).

Human Taste Test:

Flavored Water+Sucralose=water, fiber, strawberry flavor, citric acid, sucralose, acesulfame K. A triangle test with Flavored water (strawberry) control in 100 ppm sucralose with 12 ppm AceK vs. Flavored water (strawberry) in 50 ppm sucralose with (29.35 μM) 6.8 ppm COMPOUND A. Panelists evaluate two flavored water sweet solutions in a triangle taste test procedure. They are given three samples, two of which contain the same solution, and are instructed to select the sample that is different. They perform a total of two triangle tests: Flavored water (strawberry) control in 100 ppm sucralose with 12 ppm AceK vs. Flavored water (strawberry) in 50 ppm sucralose with (29.35 μM) 6.8 ppm COMPOUND A.

Conclusions:

Panelists were unable to perceive a significant difference between Flavored water (strawberry) control in 100 ppm sucralose with 12 ppm AceK vs. Flavored water (strawberry) in 50 ppm sucralose with (29.35 μM) 6.8 ppm COMPOUND A.

Two panelists correctly identified the different sample in both triangle tests.

Of the panelists who correctly identified the different sample, most indicated that it was difficult to discriminate the different sample. The removal of Acesulfame Potassium also reduces or eliminates the bitter or off taste from the drink.

TABLE XIV

Triangle test results for 100 ppm sucralose with 12 ppm AceK vs. Flavored water (strawberry) in 50 ppm sucralose with (29.35 μM) 6.8 ppm COMPOUND A. n = 22 (11 panelists × 2 reps).

| Samples | Test 1 | Test 2 | Total |
|---|---|---|---|
| Flavored Water + 100 ppm Sucralose | 7 | 7 | 14 |
| Flavored Water + 50 ppm Sucralose | 4 | 4 | 8 |
| Total | 11 | 11 | 22 |
| Confidence | 0.473 | 0.473 | 0.540 |
| Significance | 0.527 | 0.527 | 0.460 |

Example 9

Vanilla Frozen Dairy Dessert

Vanilla frozen dairy dessert was prepared using the following ingredients and evaluated for sweetness and/or lingering taste. Composition (m) comprising 50% sucralose and 6.6 ppm of 4-amino-5,6-dimethylthieno[2,3-d]pyrimidine-2(1H)-one hydrochloride had approximately the same sweetness as composition (l) which comprised 100% sucralose.

TABLE XV

| Ingredients | Sample weight (grams) 100% sucralose vanilla frozen dairy dessert (l) | Sample weight (grams) 50% sucralose vanilla frozen dairy dessert (m) |
|---|---|---|
| Low fat milk (1%) | 78.37025 | 78.37775 |
| Maltitol powder | 9.90000 | 9.90000 |
| Wheat Dextrin | 7.50000 | 7.50000 |
| Whey powder | 2.45000 | 2.45000 |
| Maltodextrin | 1.20000 | 1.20000 |
| Stabilizer | 0.40000 | 0.40000 |
| Sucralose | 0.01250 | 0.00625 |
| Acesulfame Potassium | 0.00125 | 0.00000 |
| Vanilla flavor | 0.10000 | 0.10000 |
| Propylene glycol | 0.06600 | 0.0000 |
| Compound A (1% in Propylene Glycol) | 0.00000 | 0.06600 |
| Total Weight | 100.00000 | 100.00000 |

4-amino-5,6-dimethylthieno[2,3-d]pyrimidine-2(1H)-one will be approximately 6.6 ppm as consumed (½ cup vanilla frozen dairy dessert).

Human Taste Test:

Two human tasters were used in the taste test. Paired Comparison Test with a Full Sucralose+AceK vanilla frozen dairy dessert and 50% Sucralose (no AceK)+6.6 ppm (28.49 μM) Compound A vanilla frozen dairy dessert. Panelists evaluated 2 frozen dairy desserts in a paired comparison taste test procedure. Panelists performed 2 tests each. They were instructed to select the sweeter of the two samples. They were also asked to comment on how difficult it was to tell the difference in sweetness between both samples and if any off tastes were perceived.

Product:

Full Sucralose+AceK vanilla frozen dairy dessert and 50% Sucralose (no AceK)+6.6 ppm (28.49 μM) Compound A vanilla frozen dairy dessert.

Conclusions:

Panelists found 50% Sucralose (no AceK)+6.6 ppm (28.49 μM Compound A vanilla frozen dairy dessert was not significantly different in sweetness than Full Sucralose+AceK vanilla frozen dairy dessert (p>0.05). 14 out of 26 tests indicated 50% Sucralose (no AceK)+6.6 ppm (28.49 μM) Compound A vanilla frozen dairy dessert was the sweeter sample.

3/13 panelists chose 50% Sucralose (no AceK)+6.6 ppm (28.49 μM) Compound A vanilla frozen dairy dessert as the sweeter sample in two paired comparisons.

8/13 panelists chose 50% Sucralose (no AceK)+6.6 ppm (28.49 μM) Compound A vanilla frozen dairy dessert as the sweeter sample in one paired comparison.

2/13 panelists chose 50% Sucralose (no AceK)+6.6 ppm (28.49 μM) Compound A vanilla frozen dairy dessert as the sweeter sample in zero paired comparisons.

Panelists found the test very difficult and did not detect any off-tastes.

The removal of Acesulfame Potassium also reduces or eliminates the bitter or off taste from the dairy frozen dessert.

TABLE XVI

Sample selected as more sweet by panelists. n = 26 (13 panelists × 2 reps).

| Samples | Total |
|---|---|
| Full Sucralose + AceK Vanilla Frozen Dairy Dessert | 12 |
| 50% Sucralose (no AceK) + 6.6 ppm (28.49 μM) Compound A Vanilla Frozen Dairy Dessert | 14 |
| Total | 26 |
| 50% Sucralose (no AceK) + 6.6 ppm (28.49 μM) Compound A Vanilla Frozen Dairy Dessert (p-value) | 0.845 |

Example 10

Preparation of Solutions of 4-amino-5,6-dimethylthieno[2,3-d]pyrimidine-2(1H)-one In edible compositions, above, 4-amino-5,6-dimethylthieno[2,3-d]pyrimidine-2(1H)-one (or salts, solvates, and/or esters thereof) may be added in a stable, liquid diluted form because of its potency. This form improves the use of the enhancer in testing or commercial applications. Preparation procedure of the liquid diluted form:

1. Weigh desire amount of compound.
2. Calculate the volume of food grade solvent(s) (water, Ethyl Alcohol, Isopropyl Alcohol, Butylene Glycol, Glycerol, vegetable oils (soy, corn, peanut, persic, cottonseed, sesame), fractionated coconut oil, triacetin, tributyrin, mono and diglycerides, ethyl lactate, ethyl levulinate, butyl stearate, triethyl citrate, diethyl succinate, diethyl malonate, acetic acid, lactic acid, benzyl alcohol, tetrahydrofurfural alcohol, D-limonene, γ-valeralactone, butyrolactone, Tween) to add to the dry, weighed out compound to make a concentration of 1,000-50,000 ppm (0.1-5%).
3. Pre heat the appropriate amount of solvent to 160° F. while stirring at 1,100 rpm on a hot plate using a stir bar.
4. Add pre-weighed compound to heated solvent (when temperature reaches 160° F.).
5. Continue heating solvent and inspect to insure complete dissolution, return to the hot plate if necessary.

In one embodiment, the solution contains 1% 4-amino-5,6-dimethylthieno[2,3-d]pyrimidine -2(1H)-one in propylene glycol.

| Ingredients | Percentage |
|---|---|
| Propylene Glycol | 99.00000 |
| 4-amino-5,6-dimethylthieno[2,3-d]pyrimidine-2(1H)-one hydrochloride | 01.00000 |
| Total | 100.00000 |

Example 11

Sweetness Delivery Profile Study 6 panelists evaluated two aqueous sucralose compositions (100 ppm sucralose, 50 ppm sucralose+2.0 ppm 4-amino-5,6-dimethylthieno[2,3-d]pyrimidine-2(1H)-one hydrochloride) for sweetness delivery profile. The panelists compared 3 pairs of randomized samples, and were asked to pick the samples with a taster onset of sweetness and reduced linger of sweetness. All of the panelists rated the 50 ppm sucralose+2 ppm of 4-amino-5,6-dimethylthieno[2,3-d]pyrimidine-2(1H)-one hydrochloride solutions to have a shorter linger of sweetness delivery, and 3 panelists rated the 50 ppm sucralose+2 ppm of 4-amino-5,6-dimethylthieno[2,3-d]pyrimidine-2(1H)-one hydrochloride solution to have a faster onset of sweetness delivery.

Example 12

Sugar Free Strawberry Yogurt

TABLE XVII

| Ingredients | Sample weight (grams) 100% sucralose sugar free strawberry yogurt | Sample weight (grams) 50% sucralose + 11 ppm sugar free strawberry yogurt |
|---|---|---|
| Frozen Strawberries | 6.84 | 6.84 |
| Rezista, Modified Food Starch | 0.81 | 0.81 |
| Cellulose Gum | 0.018 | 0.018 |
| Potassium Sorbate | 0.009 | 0.009 |
| Sucralose | 0.022 (216 ppm) | 0.011 (108 ppm) |
| Strawberry Flavor | 0.108 | 0.108 |
| Water | 10.193 | 10.19 |
| Plain Fat Free Yogurt | 82.00 | 81.904 |
| Compound A (1% in Propylene Glycol) | 0.00 | 0.11 |
| Total Weight | 100.00000 | 100.00000 |

Human Taste Test:

Paired comparison taste test with Strawberry Yogurt with 216 ppm Sucralose vs. Strawberry Yogurt with 108 ppm Sucralose+11 ppm Compound A Procedure:

Panelists evaluate two yogurt samples in a paired comparison taste test procedure and are instructed to select the sweeter of the two samples. They perform a total of three paired comparison tests each containing the following samples: Strawberry Yogurt with 216 ppm Sucralose vs. Strawberry Yogurt with 108 ppm Sucralose+11 ppm Compound A.

Products:
  Strawberry Yogurt=Frozen Strawberry, modified food starch, cellulose gum, potassium sorbate, sucralose, strawberry flavor, water, fat-free plain yogurt, heated propylene glycol, optional Compound A Conclusions:
  Panelists found Strawberry Yogurt with 216 ppm Sucralose was not significantly different in sweetness than Strawberry Yogurt with 108 ppm Sucralose+11 ppm Compound A (p<0.05). 22 of 42 tests indicated Strawberry Yogurt with 108 ppm Sucralose+11 ppm Compound A was the sweeter sample.
  4/14 panelists chose Strawberry Yogurt with 108 ppm Sucralose+11 ppm Compound A as the sweeter sample in all three of the paired comparison tests. 3/14 panelists chose Strawberry Yogurt with 216 ppm Sucralose as the sweeter sample in all three of the paired comparison tests.

TABLE XVIII

Sample selected as sweeter by panelists: Strawberry Yogurt with 216 ppm Sucralose vs. Strawberry Yogurt with 108 ppm Sucralose + 11 ppm Compound A. n = 42 (14 panelists × 3 reps).

| Samples | Test 1 | Test 2 | Test 3 | Total |
|---|---|---|---|---|
| Strawberry Yogurt with 216 ppm Sucralose | 8 | 4 | 8 | 20 |
| Strawberry Yogurt with 108 ppm Sucralose + 11 ppm Compound A | 6 | 10 | 6 | 22 |
| Total | 14 | 14 | 14 | 42 |
| Strawberry Yogurt with 108 ppm Sucralose + 11 ppm Compound A selected (p-value) | >0.791 | 0.180 | >0.791 | 0.878 |

Example 13

Synthesis of 2-amino-4,5-dimethylthiophene-3-carbonitrile

A solution of 3-mercapto-2-butanone (1.00 kg, 9.0 mole, 93.6% assay) in 2.0 L SDA 3C 200 Proof, absolute Ethanol (Ethanol) is prepared in a 5 L 1N RBF fitted with torian and transfer tubing. Malononitrile (588.8 g, 8.9 mole) is dissolved in 5.0 L Ethanol and cooled to 4° C. at which point triethylamine (250 mL, 1.8 mole, 0.2 equivalent) is added with a 560 mL ethanol rinse. The anionic malononitrile solution is cooled to −2° C. and the 3-mercaptobutanone solution is added over 1.3 hrs at −1 to −5° C. After an hour, the reaction shows less than 0.1% malononitrile. The reaction is concentrated on the rotovap (40° C. bath) to a slurry of approximately 2.5 L and 3.0 L of heptanes are added. The slurry is cooled to 5° C. for 30 minutes and the solids collected by filtration. The solids are rinsed with 2.5 L of 20% Ethanol in heptanes in 7 portions. The excess solvent is removed on the filter, and the wet cake dried in a vacuum oven overnight at 40° C. and full vacuum to give an off white solid as 2-amino-4,5-dimethylthiophene-3-carbonitrile (870 g, 64.1% yield, 99.7% purity shown by HPLC). The filtrates are re-concentrated to an oily slurry which is filtered and rinsed with 0.5 L of 20% Ethanol in heptanes. The second crop of solids is dried separately (47 g, 3.5% yield, 98.6% purity shown by HPLC). $^1$H NMR (400 MHz, DMSO-$d_6$) δ 1.93 (d, J=1.2 Hz, 3H), 2.07 (d, J=1.2 Hz, 3H), 3.33 (s, 2H). MS 153 (MH$^+$). HPLC Retention Time: approximately 10.9 minute (Phenomenex Luna C18 (2) column, acetonitrile/water with 0.1% AcOH).

2-Mercapto-3-butanone can be readily made from 2-butanone, sulfur, ammonia in high yields as described in U.S. Pat. No. 2,888,487, and shown in Scheme 2 below.

Scheme 2

The terms "a" and "an" do not denote a limitation of quantity, but rather denote the presence of at least one of the referenced item. The term "or" or "and/or" is used as a function word to indicate that two words or expressions are to be taken together or individually. The terms "comprising", "having", "including", and "containing" are to be construed as open-ended terms (i.e., meaning "including, but not limited to"). The endpoints of all ranges directed to the same component or property are inclusive and independently combinable.

While the present invention has been particularly shown and described with respect to preferred embodiments thereof, it will be understood by those skilled in the art that the foregoing and other changes in forms and details may be made without departing from the spirit and scope of the invention. It is therefore intended that the present invention not be limited to the exact forms and details described and illustrated but fall within the scope of the appended claims.

We claim:

1. A process of preparing a compound having structural Formula (a):

(a)

comprising:
  mixing a compound having structural Formula (b):

(b)

with a compound having structural Formula (c):

(c)

in the presence of an organic amine at a temperature of about 0° C. or below to obtain a reaction mixture;
  maintaining the reaction mixture at a temperature of about 0° C. or below for about 30 to about 90 minutes;

concentrating the reaction mixture to obtain a slurry; and
filtering the slurry to obtain the compound having structural Formula (a) as solid particles;
wherein:
$R^1$ is hydrogen, alkyl, heteroalkyl, aryl, heteroaryl, arylalkyl, or heteroarylalkyl;
$R^2$ is hydrogen, alkyl, heteroalkyl, alkenyl, aryl, heteroaryl, arylalkyl, or heteroarylalkyl;
or alternatively, $R^1$ and $R^2$, together with the atoms to which they are attached, form a carbocyclic ring or heterocyclic ring;
X is CN or —C(O)$R^3$;
$R^3$ is alkyl, aryl, heteroaryl, arylalkyl, heteroarylalkyl, $OR^4$, or $N(R^4)_2$; and
each $R^4$ is independently hydrogen, alkyl, aryl, heteroaryl, arylalkyl, or heteroarylalkyl.

2. The process of claim 1, further comprising:
washing the solid particles of the compound having structural Formula (a) with an eluting solvent, wherein the eluting solvent is a mixture of an alcohol solvent and an alkane hydrocarbon solvent.

3. The process of claim 1, wherein the volume ratio of the alcohol solvent to the alkane hydrocarbon solvent is from about 1:9 to about 1:3.

4. The process of claim 1, wherein the mixing step comprises:
adding an alcohol solution of the compound having structural Formula (b) to an alcohol solution of the compound having structural Formula (c) and the organic amine at a temperature of about 0° C. or below.

5. The process of claim 1, wherein the molar ratio of the compound having structural formula (b) to the compound having structural formula (c) is from about 1:0.9 to about 1:1.1.

6. The process of claim 1, wherein the molar ratio of the compound having structural formula (c) to the organic amine is from about 5.1:1 to about 4.9:1.

7. The process of claim 1, wherein
$R^1$ is hydrogen or alkyl;
$R^2$ is hydrogen or alkyl; and
X is CN.

8. The process of claim 1, wherein
$R^1$ is methyl;
$R^2$ is methyl; and
X is CN.

* * * * *